United States Patent [19]
Blechman et al.

[11] Patent Number: 4,507,084
[45] Date of Patent: Mar. 26, 1985

[54] PALATAL EXPANSION DEVICE

[75] Inventors: Abraham Blechman, Tappan, N.Y.; Eugene A. Pescatore, Elmwood Park, N.J.

[73] Assignee: Medical Magnetics, Inc., Ramsey, N.J.

[21] Appl. No.: 560,878

[22] Filed: Dec. 13, 1983

[51] Int. Cl.³ .............................................. A61C 7/00
[52] U.S. Cl. ...................................................... 433/7
[58] Field of Search ................................... 433/6, 7, 18

[56] References Cited
U.S. PATENT DOCUMENTS
3,984,915 10/1976 Noble ..................................... 433/18
4,026,023 5/1977 Fisher ..................................... 433/7

Primary Examiner—Robert Peshock
Attorney, Agent, or Firm—Hopgood, Calimafde, Kalil, Blaustein & Judlowe

[57] ABSTRACT

The invention contemplates an orthodontic palatal expansion device wherein separate palate-body halves are attachable to adjacent maxillary teeth and incorporate permanent magnets arranged in a repulsion mode and mounted in such a way as to apply force needed to split the mid-palatal suture. The reacting fields of these magnets also aid in reorganization of the tissues to insure maintenance of the expansion and to accelerate osteogenesis. The device may be constructed for fixation to the patient, as via orthodontic bands, or it may be fashioned with orthodontic wires that permit selective removal and replacement by the patient.

13 Claims, 4 Drawing Figures

PALATAL EXPANSION DEVICE

BACKGROUND OF THE INVENTION

The invention relates to an orthodontic device applicable to the lingual side of teeth of the maxillary arch for applying laterally spreading force to establish a split or a resetting of the mid-palatal suture. The device may also be applied in the treatment of cleft-palate patients, as for example in the lateral positioning of premaxilliary and maxillary fragments.

In the present state of the art, palatal-expansion devices with adjustable clamps are available to apply spreading pressure to teeth of the right and left halves of the maxillary arch. And these devices require frequent resetting by the orthodontist as the suture yields and the halves of the arch progressively displace. The forces are positive and are positively set, giving rise to pain upon each adjustment; after plural adjustment, a total displacement may be in the order of a quarter inch, and as many as ten visits to the orthodontist may be involved in making the requisite progressive adjustments.

BRIEF STATEMENT OF THE INVENTION

It is an object of the invention to provide improved orthodontic means of the character indicated.

A specific object is to provide means to meet the above object without requiring the frequency of patient visits or the overall time period previously regarded as necessary to achieve a given spread of the halves of the maxillary arch.

It is another specific object to meet the above objects using the repulsive force of reacting polarized magnets to achieve continuous force application.

A general object is to meet the above objects with structure which may be worn by the patient with minimum discomfort.

The invention achieves the above objects in a palatal expansion device wherein separate lateral body halves are attachable to adjacent maxillary teeth and incorporate permanent magnets arranged in a repulsion mode and mounted in such a way as to apply force needed to split the mid-palatal suture. The reacting fields of these magnets also aid in reorganization of the tissues to insure maintenance of the expansion and to accelerate osteogenesis. The device may be constructed for fixation to the patient, as via orthodontic bands, or it may be fashioned with orthodontic wires that permit selective removal and replacement by the patient.

DETAILED DESCRIPTION

The invention will be illustratively described in detail, for various embodiments, in conjunction with the accompanying drawings, in which.

Figure 1:
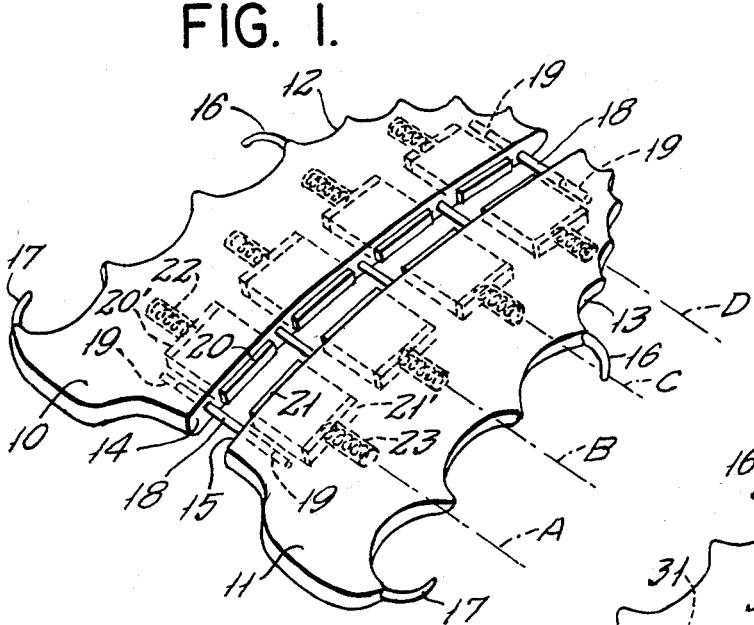
FIG. 1 is a view in perspective of a first embodiment, with some exaggerations to permit greater clarity.

In FIG. 1, a palatal-expansion device of the invention is seen to comprise separate lateral halves 10-11 of a body, separated along a longitudinal midline and having outer-edge contouring 12-13 which conforms to the lingual side of teeth of the respective halves of a maxillary arch. Preferably, the body is made by conventional impression techniques and is therefore a custom fit to the patient; after formative processing, suitably with a biocompatible acrylic material, the molded body is cut along the midline to define the separate body halves 10-11, with mutually facing central edge faces 14-15. Anchoring devices may be carried at molar and premolar regions of outer edges 12-13 for acceptance of orthodontic bands, but in the form shown, orthodontic clasps 16-17 are provided for removable reference to such teeth.

In accordance with the invention, one or more pairs of permanent magnets, arranged in repulsive mode, are carried by the body parts 10-11 and are oriented for lateral application of the repulsion forces to the respective body parts. Four pairs of such magnets are shown in the device of FIG. 1; the magnets may be any one of a variety of shapes and proportions, but in the form shown all individual magnets are of thin rectangularly prismatic shape, guided for limited lateral displaceability and spring-urged to like-pole confrontation along the central or midline edges 14-15. Also, guide means in the form of plural spaced lateral rods 18, as of stainless steel, slidable in opposed pairs of aligned guide bores 19 in the respective body halves 10-11 assure magnet-pole alignment and a major degree of overall body integrity as well as a significant range of lateral displaceability of the body parts 10-11.

More specifically, a first pair of magnets on transverse alignment A comprises a first magnet 20 guided for lateral displaceability in a lateral bore 20' in body part 10, and a second magnet 21 similarly guided for lateral displaceability in a lateral bore 21' in body part 11. Captive in a further bore behind each of the magnets (and on alignment A) is a compressionally loaded orthodontic spring (22 in part 10, 23 in part 11) providing force to keep the adjacent opposed pole faces of magnets close together. It has been explained that FIG. 1 includes some exaggeration, and it will be understood that, necessarily, the described relation places edge faces 14-15 and the magnet pole faces closer together than shown in the drawing. Various permanent-magnet materials are available for use at 20-21, but we state our present preference for SmCo, as well as our preference that each magnet be protively coated with biocompatible material, such as an acrylic, or an epoxy, or an electroplated layer.

What has been said as to magnets 20-21 and their mounting on alignment A applies also for the respective pairs of like magnets and associated preloading means at each of the further transverse alignments B-C-D in spaced relation along the central edges 14-15. Also, if desired, further provision for guidance may be available from further guide rods and bores 18-19 at locations between magnet alignments. And it will be understood that, for unit-handling retention purposes, a suitable detachable fastener or lost-motion restraint, (not shown), may be provided as between the body halves 10-11.

Figure 2:
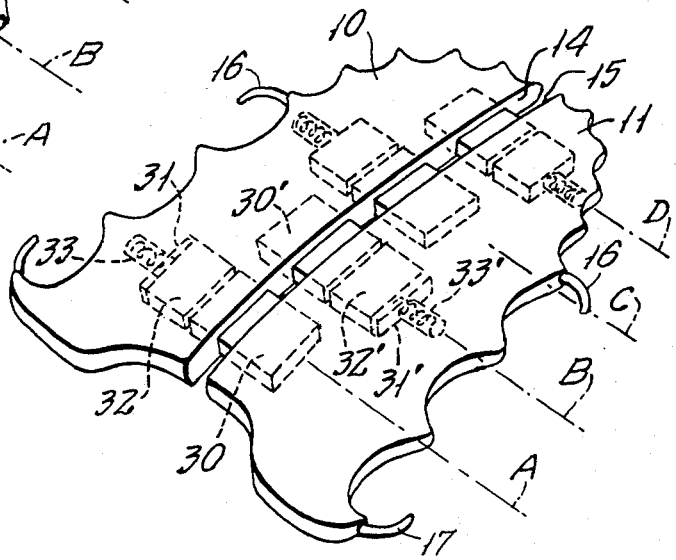
FIGS. 2 and 3 are views similar to FIG. 1, for two further embodiments.

In the embodiment of FIG. 2, separate halves 10-11 of the body will again be recognized, as also will the spaced transverse alignments A-B-C-D of pairs of permanent magnets, in repulsion-mode array. However, in FIG. 2, reliance is placed on one magnet of each pair to be permanently fixed in its body half and to project beyond the central edge of its body half for laterally guided displaceability in an aligned guide bore of the other body half. Thus, on alignment A in FIG. 2, a first magnet 30 is fixedly mounted in body part 11 and projects into guided relation with a deep bore 31 in body part 10. The deep bore 31 fully accommodates the other magnet 32 of the reacting pair (30, 32), and magnet 32 is not only guided for lateral displacement in bore 31 but is also preloaded by a compressionally preloaded orthodontic spring 33 in the direction toward magnet 30. Opposed pairs of repulsion magnets at alignments B-C-D have descriptions as given for magnets 30-32 on alignment A, except for interlaced reversal of the fixed and movable magnet locations. Thus, on alignment C, the fixed and movable magnets and their preloading are as described for alignment A; and on alignments B and D, the fixed magnet (30') is carried by the body half 10 and has guided displaceability in the guide bore 31' for the movable magnet 32', while the preload spring 33' acting on magnet 32' is captive in body part 11. No guide rods 18 or bores 19 are needed, in view of the guide functions of fixed magnets 30 (30').

Figure 3:
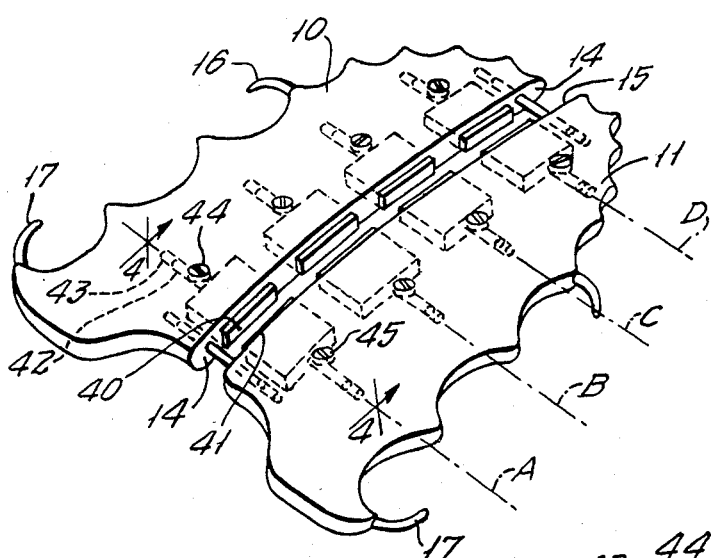
Figure 4:
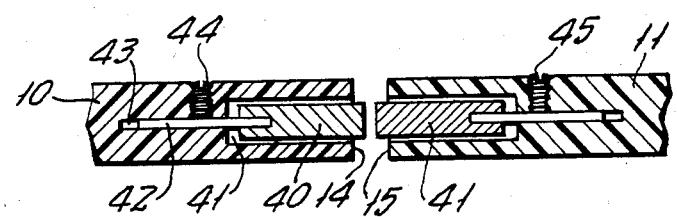
FIG. 4 is an enlarged fragmentary sectional view, taken at 4—4 in FIG. 3.

In the embodiment of FIGS. 3 and 4, opposed pairs of magnets again react repulsively on each of the plurality of transverse alignments A-B-C-D, and guide-rod and bore means 18-19 are provided as in FIG. 1. As best seen in FIG. 4, magnet 40 carried in a guide bore 41 in body part 10 has its own guide-stem or tail rod 42 (as of stainless steel) which is in turn guided in a suitable deeper bore 43 in part 10. An orthodontic lock, symbolized by an externally accessible set screw 44, enables rod 42 to be adjustably secured for different degrees of magnet (40) projection beyond the midline face of body part 15. And what has been said as to such adjustable setting of magnet 40 applies equally for the adjustability of magnet 41 via its orthodontic lock device 45. With the arrangement of FIG. 3, it is thus possible to adjust all magnet projections, as may be determined to be best for repulsion-force development at any one or at all alignments A-B-C-D.

The described embodiments will be seen to have achieved all stated objects. In every case the smooth and continuously applied magnetic-repulsion force is effective to produce relatively rapid palatal expansion, because the force, which may be in the order of 300 or more grams of repulsion, is constantly applied and will continue even though spreading displacement has taken place. The protective coating of magnets assures against incompatibility with body fluids, and if desired for further such assurance, the magnets which are relied upon for a guidance function (as in FIG. 2) may be protected by stainless-steel sleeve enclosure, prior to biocompatible coating, as disclosed in copending patent application Ser. No. 322,423, filed Nov. 18, 1981. Generally speaking, the maximum thickness of body parts 10-11 is about 4 millimeters and is sufficient for guided accommodation of magnets which are 2 millimeters thick. Of course, the body parts 10-11 reduce and are tapered and faired as needed for the patient's better tolerance and comfort.

While the invention has been described in detail for preferred and illustrative embodiments, it will be understood that modifications may be made without departing from the scope of the invention.

What is claimed is:

1. An orthodontic device for rapid palatal expansion of a maxillary arch, comprising two palate body parts constituting right and left longitudinally divided halves of a body, said body parts having adjacent longitudinally extending central confronting edges and having outer edges in general conformance with the lingual contouring of teeth of the respective right and left halves of a maxillary arch, guide means including aligned coacting formations in said adjacent edges of the respective body parts, said guide means establishing a degree of relative lateral displaceability of said body parts with respect to each other, and means including a polarized magnet carried by each of said body parts, said magnets being in like-pole confronting relation, whereby repulsion-force reaction between said magnets is operative to constantly urge outward lateral displacement of said body parts.

2. The orthodontic device of claim 1, in which an orthodontic wire is embedded in each body part and is exposed along at least part of said outer edges for positive anchorage to one or more teeth of the maxillary arch.

3. The orthodontic device of claim 1, in which said guide means includes aligned transverse bores in said body parts, and a guide wire entered in common to said aligned bores.

4. The orthodontic device of claim 1, in which said guide means includes aligned transverse bores in said body parts, a first of said magnets being fully received in one of said bores, and the second of said magnets being partly received in said one bore and partly received in the other of said bores and therefore contributing to the retained alignment of said bores.

5. The orthodontic device of claim 4, in which a compression spring is captive in one of said bores behind one of said magnets and is preloaded to urge the same toward the other magnet.

6. The orthodontic device of claim 4, in which compression-spring means is captive in each of said bores behind each of the respective magnets and is preloaded to urge the magnets toward each other.

7. The orthodontic device of claim 1, in which at least one of said body parts has a laterally extending guide bore open at the central edge of said body part, said guide bore being configured for laterally displaceable guidance of the magnet of said one body part, and a compression spring captive in said bore behind the magnet, said spring being preloaded to urge the magnet of said one body part in the direction of the magnet of the other body part.

8. The orthodontic device of claim 1, in which each body part has a laterally extending guide bore open at the central edge of the body part, said guide bores being configured for laterally displaceable guidance of the associated magnet, and a compression spring captive in each bore behind the associated magnet, said springs being preloaded to urge the respective magnets toward each other.

9. The orthodontic device of claim 1, in which at least one of said body parts has a laterally extending guide bore open at the central edge of said body part, said guide bore being configured for laterally displaceable guidance of the magnet of said one body part, and orthodontic-clamp means carried by said one body with externally accessible actuating means for clamping a selected lateral position of the magnet in said guide bore.

10. The orthodontic device of claim 1, in which each body part has a laterally extending guide bore open at the central edge of the body part, said guide bores being configured for laterally displaceable guidance of the associated magnet, and orthodontic-clamp means carried by each body part with externally accessible actuating means for clamping a selected lateral position of the associated magnet in its guide bore.

11. The orthodontic device of claim 1, in which said magnets constitute the first of a plurality of opposed pairs of magnets in like-pole confronting relation and at longitudinally spaced locations along the central edges.

12. The orthodontic device of claim 3, in which said aligned transverse bores and associated guide wire constitute one of a plurality of pairs of aligned transverse bores with an associated guide wire entered in common to each pair of aligned bores.

13. The orthodontic device of claim 1, in which each of said body parts includes means for outer-edge fixed anchorage to molar and/or premolar teeth.

* * * * *